(12) United States Patent
Kidwell

(10) Patent No.: US 11,340,217 B2
(45) Date of Patent: May 24, 2022

(54) CATALYTIC PARTICLES FOR INCREASED SENSITIVITY IN LATERAL FLOW IMMUNOASSAYS

(71) Applicant: The Government of the United States of America, as represented by the Secretary of the Navy, Arlington, VA (US)

(72) Inventor: David A. Kidwell, Alexandria, VA (US)

(73) Assignee: The Government of the United States of America, as represented by the Secretary of the Navy, Washington, DC (US)

(*) Notice: Subject to any disclaimer, the term of this patent is extended or adjusted under 35 U.S.C. 154(b) by 312 days.

(21) Appl. No.: 15/455,045

(22) Filed: Mar. 9, 2017

(65) Prior Publication Data

US 2018/0052153 A1 Feb. 22, 2018

Related U.S. Application Data

(60) Provisional application No. 62/305,877, filed on Mar. 9, 2016.

(51) Int. Cl.
*G01N 33/558* (2006.01)
*G01N 33/53* (2006.01)
*G01N 33/543* (2006.01)
*G01N 11/02* (2006.01)
*G01N 33/532* (2006.01)

(52) U.S. Cl.
CPC ........ *G01N 33/5306* (2013.01); *G01N 11/02* (2013.01); *G01N 33/532* (2013.01); *G01N 33/54306* (2013.01); *G01N 33/54333* (2013.01); *G01N 33/54346* (2013.01); *G01N 33/54353* (2013.01); *G01N 33/54387* (2021.08); *G01N 33/54388* (2021.08); *G01N 33/54393* (2013.01); *G01N 33/558* (2013.01)

(58) Field of Classification Search
CPC ........ G01N 33/5306; G01N 33/54353; G01N 33/532; G01N 33/54306; G01N 33/54333; G01N 33/54393; G01N 33/54346; G01N 11/02; G01N 33/558; G01N 33/54387; G01N 33/54388

USPC ....... 436/524, 525, 169, 170, 514, 530, 810; 422/400, 401, 420, 421, 425, 426, 430; 435/287.7, 287.9, 970, 805, 810

See application file for complete search history.

(56) References Cited

U.S. PATENT DOCUMENTS

| | | | |
|---|---|---|---|
| 4,313,734 A * | 2/1982 | Leuvering | G01N 33/553 422/400 |
| 5,196,302 A | 3/1993 | Kidwell | |
| 5,200,321 A | 4/1993 | Kidwell | |
| 5,248,772 A * | 9/1993 | Siiman | G01N 33/548 536/112 |
| 5,369,007 A | 11/1994 | Kidwell | |
| 5,384,265 A | 1/1995 | Kidwell et al. | |
| 5,637,508 A | 6/1997 | Kidwell et al. | |
| 6,730,230 B2 * | 5/2004 | Cook | G01N 33/54313 210/222 |
| 7,935,541 B2 * | 5/2011 | Chiku | G01N 33/558 435/7.1 |
| 2007/0207335 A1 * | 9/2007 | Karandikar | C09D 7/67 428/560 |
| 2010/0021954 A1 * | 1/2010 | Deshayes | B82Y 30/00 435/29 |

OTHER PUBLICATIONS

McKenzie, "Glutaraldehyde and reduction techniques for immunolabeling", posted Oct. 31, 2015 at http://www.brainpreservatiion.org/glutaraldehyde-and-reduction-techniques-for-immunolabeling/.*
Mayes, Biomolecular Sensors, 2002, pp. 65-70. (Year: 2002).*
Conyers et al., "Chromogenic Substrates for Horseradish Peroxidase," Analytical Biochemistry, 192, 207-211 (1991).

* cited by examiner

*Primary Examiner* — Christopher L Chin
(74) *Attorney, Agent, or Firm* — US Naval Research Laboratory; Rebecca L. Forman

(57) ABSTRACT

The present invention provides a method for preparing colloidal palladium nanoparticles and using them for increased sensitivity in lateral flow immunoassays. Glutaraldehyde is used in preparing the colloidal palladium that allows rapid attachment of biomolecules. Colloidal palladium nanoparticles are labeled with a protein, such as a biomolecule or an antibody. These labeled colloidal palladium particles catalytically develop a dye to detect the presence of an analyte.

9 Claims, 10 Drawing Sheets

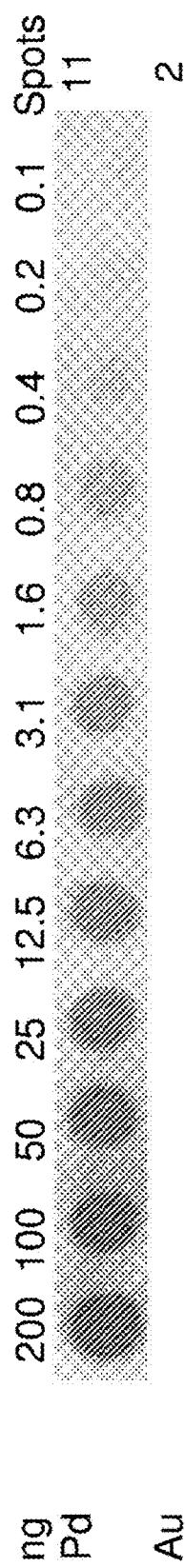
FIG. 4
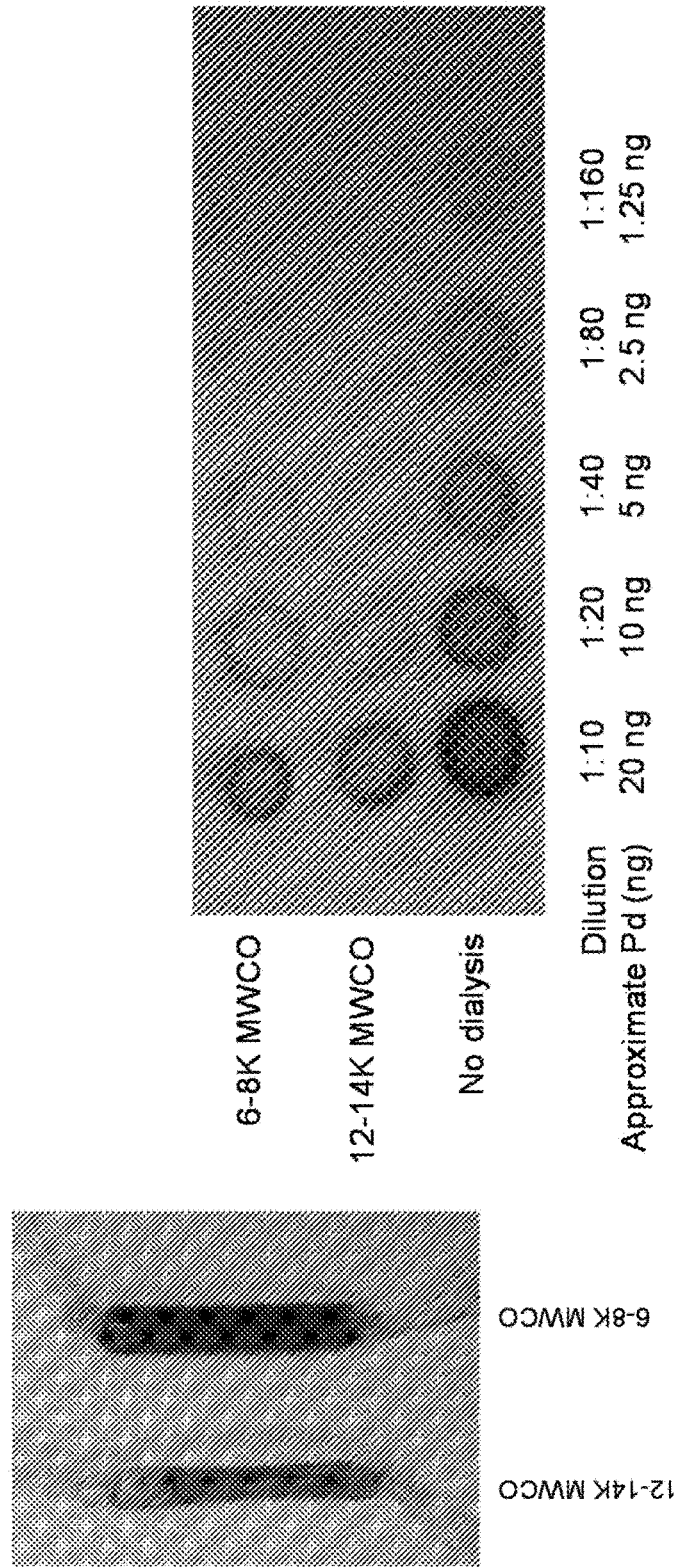
FIG. 5B
FIG. 5A

CATALYTIC PARTICLES FOR INCREASED SENSITIVITY IN LATERAL FLOW IMMUNOASSAYS

PRIORITY CLAIM

The present application is a non-provisional application claiming the benefit of U.S. Provisional Application No. 62/305,877, filed on Mar. 9, 2016 by David A. Kidwell, entitled "Catalytic Particles for Increased Sensitivity in Lateral Flow Immunoassays," the entire contents of which is incorporated herein by reference.

BACKGROUND OF THE INVENTION

Field of the Invention

The present invention relates to catalytic particles in lateral flow immunoassays.

Description of the Prior Art

Lateral flow and vertical flow paper-based immunoassays (LFIAs) are widely used as point-of-care devices for surveillance and diagnostics. An example of a LFIA is a home pregnancy test. LFIAs typically use visual labels for detection. For use in limited resource countries or in many field situations, the immunoassays must be read by the unaided eye. Several modes of operation of LFIAs are depicted in FIGS. 1-3.

FIG. 1 shows the principle of an LFIA for a sandwich assay for a large antigen. In the simplest system, a paper strip is impregnated in three areas with reagents. Nitrocellulose is typically the substrate of choice because it allows binding of the biomolecules by simple application. Nearest the application zone, a colloidal particle (gold or latex) is dried. In this example, the colloidal particle is labeled with an antibody that recognizes one epitope of an antigen. In the analysis zone, a second antibody is bound to the strip that recognizes a second epitope of the antigen of interest. Targeting a large antigen allows antibodies to bind and recognize simultaneously two parts of the antigen. In the control zone, a second antibody against the antibody labeled particle is bound. For example, if the antibody-labeled particle was a goat anti-antigen, the control line may have a rabbit anti-goat antibody. When a solution is applied, the colloidal particles are mobilized and move to the end of the strip being carried by the test solution. If antigens are present in the test solution, they form a sandwich between the two antibodies on the test line and immobilize some of the colloidal particles at that line. Often other parts are near the end of the strip that indicate successful migration and sufficient fluid being present and filters in the application zone to remove debris.

FIG. 2 shows the principle of an LFIA for a competitive assay for a small antigen. In the simplest system, a paper strip is impregnated in three areas with reagents. Nitrocellulose is typically the substrate of choice because it allows binding of the biomolecules by simple application. Nearest the application zone, a colloidal particle (gold or latex) is dried. In this example, the colloidal particle is labeled with an antibody to a drug. In the analysis zone, drugs molecules are bound. This is most often conveniently accomplished by conjugating a drug to a carrier protein, which binds non-specifically to the nitrocellulose. In the control zone, a second antibody against the antibody labeled particle is bound. For example, if the antibody-labeled particle was a goat anti-antigen, the control line may have a rabbit anti-goat antibody. When a solution is applied, the colloidal particles are mobilized and move to the end of the strip being carried by the test solution. If antigens (drugs) are present in the test solution, they inhibit the binding of the colloidal particle to the analysis zone but not to the control zone. Often other parts are near the end of the strip that indicate successful migration and sufficient fluid being present and filters in the application zone to remove debris.

FIG. 3 shows the principle of an LFIA for a competitive assay for a small antigen. In the simplest system, a paper strip is impregnated in three areas with reagents. Nitrocellulose is typically the substrate of choice because it allows binding of the biomolecules by application. Nearest the application zone for the test solution, a colloidal particle (gold or latex) is dried. In this example, the colloidal particle is labeled with a drug conjugate. In the analysis zone, an anti drug antibody is bound to the paper strip. In the control zone, a second antibody against another haptin on the colloidal particle is bound. When a solution is applied, the colloidal particles are mobilized and move to the end of the strip being carried by the test solution. If antigens (drugs) are present in the test solution, they inhibit the binding of the colloidal particle to the analysis zone but not to the control zone. Often other parts are near the end of the strip that indicate successful migration and sufficient fluid being present and filters in the application zone to remove debris.

These modes of operation are well-known in the art, for example, see U.S. Pat. No. 5,200,321 issued on Apr. 6, 1993. Most visually-read systems are based on either colloidal gold or colored latex as the visual readout. However, the color density (and hence the sensitivity) of such a system is limited to the absorbance of the particle.

Although there exists a wide variety of instrumental approaches to increase the sensitivity and improve the quantitation (i.e. enzymes, fluorescence, metals, or phosphor up-converters as labels) little can be done to enhance this sensitivity if constrained to non-aided, visual readouts. For many applications, the sensitivity of LFIAs is their biggest weakness. Enzymes are an exception to the detection scheme as they can amplify a given binding event, but they degrade during long-term storage because they are temperature and desiccation sensitive. Alternative, non-enzymatic, catalytic, amplification systems are based on silver precipitation around the gold particles, similar to photography. This is a complex process that requires several solutions and has background issues where waiting too long will actually loose signal similar to overdeveloping a photograph.

The Naval Research Laboratory has a long history in development of vertical-flow, paper-based immunoassays having pioneered the Micro-Assay on a Card (MAC Assay) for detection of drugs of abuse. (U.S. Pat. No. 5,200,321 issued on Apr. 6, 1993; U.S. Pat. No. 5,369,007 issued on Nov. 29, 1994). The MAC assay employed a multilayer laminated structure with an enzyme as the amplicon in a displacement-type assay. Much of the sensitivity was achieved through the use of enzymes and superabsorbent polymers in the detection area. (U.S. Pat. No. 5,196,302, issued on Mar. 23, 1993). Superabsorbent polymers absorb 10-100 times their weight in water (they are often used in disposable diapers), are self-buffering, and are transparent so that any developed color would be observable throughout the polymer rather than just on the surface, as in typical paper assays. Because of the use of enzymes, the MAC assay had manufacturing difficulties. To solve the manufacturing problem, catalytic particles were invented (U.S. Pat. No. 5,384,265 issued Jan. 24, 1995; U.S. Pat. No. 5,637,508 issued Jun. 10, 1997), but the application of the MAC assay to drugs of abuse detection was limited as lateral-flow assays became more widely developed and less expensive.

Using the systems described in U.S. Pat. Nos. 5,200,321 and 5,369,007 applied to palladium would produce particles that are partially black in color. These particles settle out of solution within 24 hours and are too large to migrate in a lateral flow assay. Moreover, it would not be obvious that these could be used in a lateral flow assay.

BRIEF SUMMARY OF THE INVENTION

The aforementioned problems are overcome in the present invention which provides catalytic particles based on colloidal palladium that are a direct replacement for the colloidal gold or colored latex visual labels. This system has demonstrated at least a 30 fold increase in sensitivity in test immunoassay systems over colloidal gold with only a five minute reaction time for the catalytic development.

The present invention provides a method for preparing colloidal palladium nanoparticles and their use in the rapid, catalytic preparation of a highly-colored dye at room temperature. The nanoparticles bind to proteins non-specifically—just mix and use. The results can be read by an unaided eye, which is applicable to field situations. Results can be shown in popular formats, such as two lines or +/−. The palladium nanoparticles are stable for over a year and are dryable. These particles are more stable than typical biomolecules—heat stable to at least 80° C. (in solution) and 60° C. on surfaces. EDTA can be incorporated to remove non-specific catalytic reactivity, and EDTA does not affect the activity of the nanoparticles.

Some potential applications are incorporating this technology into existing assays to make surveillance on non-symptomatic malaria carriers possible in remote locations in a convenient and rapid matter or increasing the sensitivity of fieldable assays for marijuana detection in saliva in driving under the influence testing. Additionally, it is feasible that this technology could be applied to DNA amplicons and thus expand the rapid-assay universe to DNA/RNA diseases.

These and other features and advantages of the invention, as well as the invention itself, will become better understood by reference to the following detailed description, appended claims, and accompanying drawings.

BRIEF DESCRIPTION OF THE DRAWINGS

FIG. 4 shows the visibility of developed palladium nanoparticles versus the visibility of colloidal gold.

FIG. 5A is a picture of the colloid inside dialysis tubing after dialysis. FIG. 5B shows sensitivity comparison through serial dilution.

DETAILED DESCRIPTION OF THE INVENTION

Figure 1:
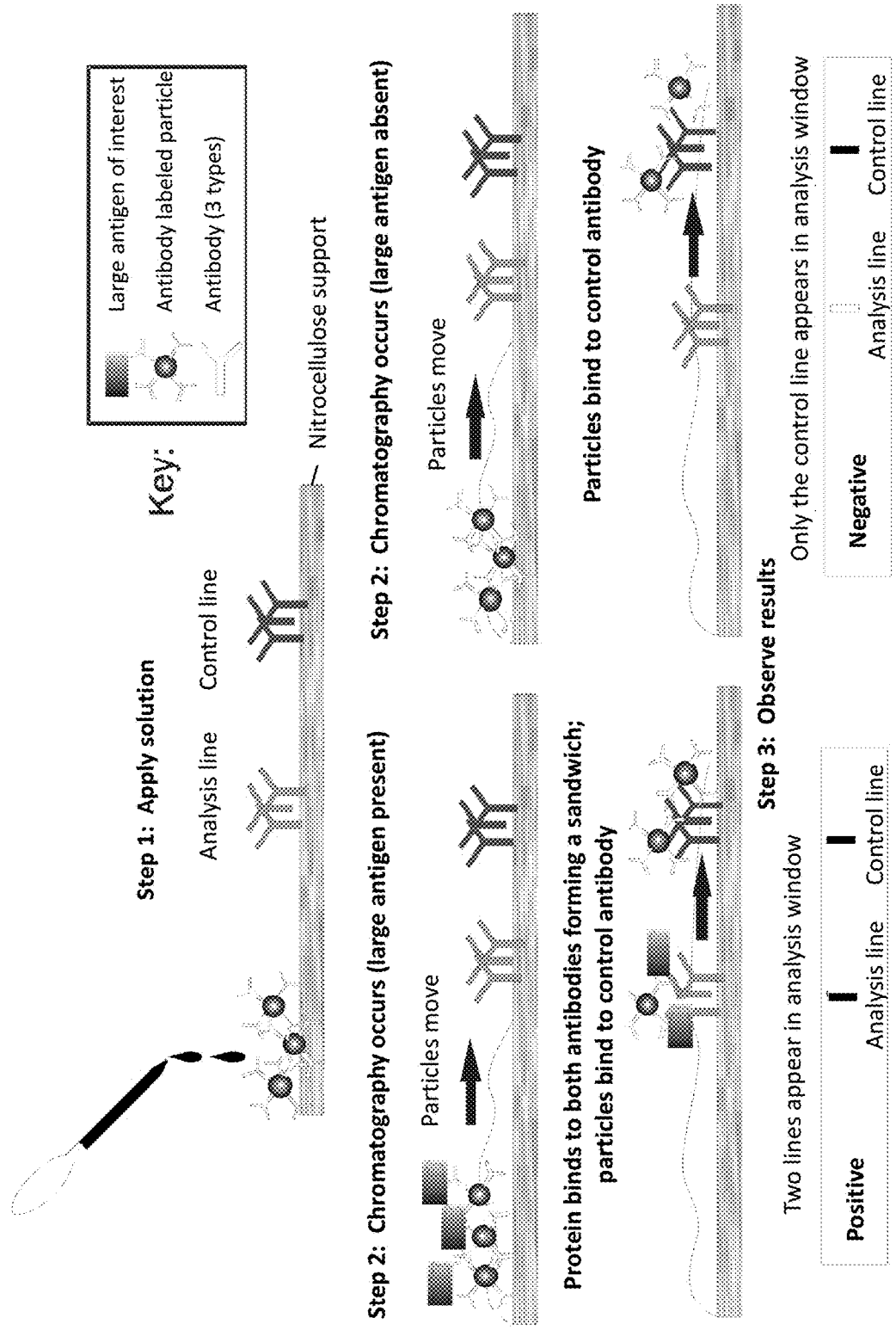
FIG. 1 is a diagram showing the principle of a LFIA for a sandwich assay for a large antigen.
Figure 2:
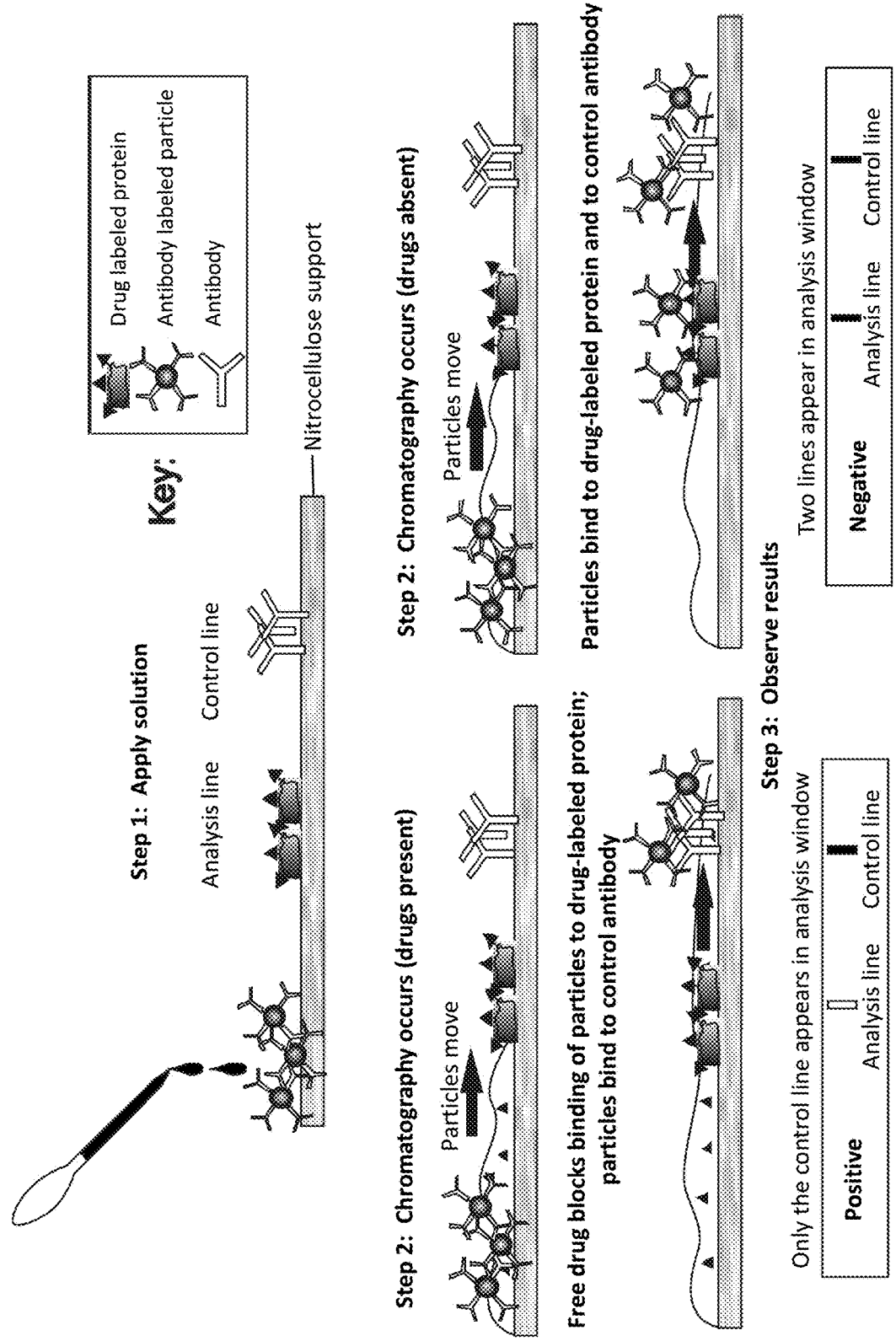
FIG. 2 is a diagram showing the principle of a LFIA for a competitive assay for a small antigen.
Figure 3:
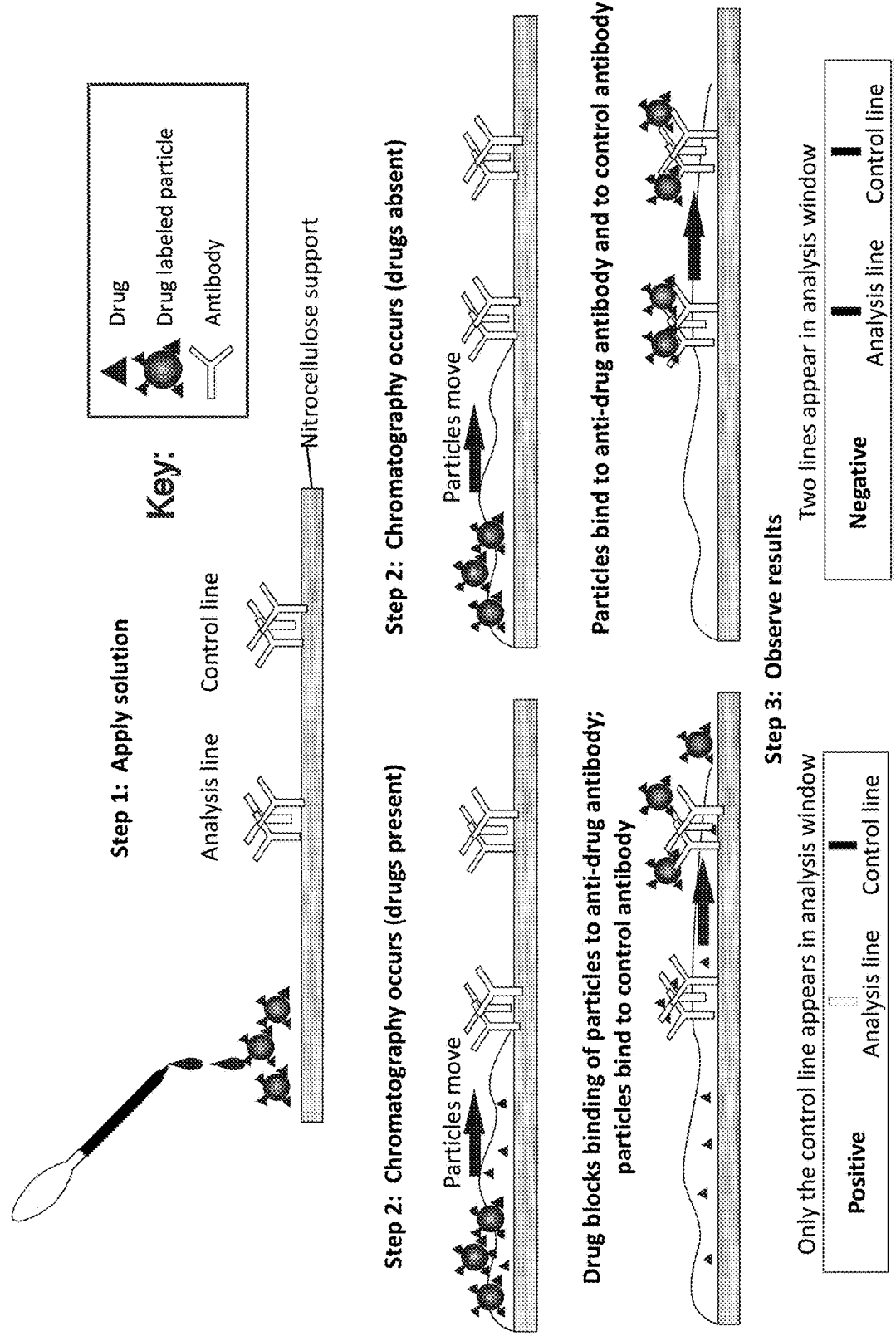
FIG. 3 is a diagram showing the principle of a LFIA for a competitive assay for a small antigen.

The present invention provides a method to prepare colloidal palladium nanoparticles and their use in the rapid, catalytic preparation of a highly-colored dye at room temperature. These particles provide increased sensitivity in lateral flow immunoassays. In preparing the colloidal palladium, an aldehyde coating is developed that does not seriously affect the activity but allows rapid attachment of biomolecules, likely through free lysines. The preparation conditions allow production of colloidal palladium of a very small and uniform size is used such that it does not precipitate from solution on storage and is mobile in a LFIA. The resultant imine linkages can be stabilized though sodium borohydride reduction.

In lateral flow immunoassays, the smaller the size of the particle the better. It is known in the art that the optimal size for gold is 20-50 nm. This is based on absorption characteristics (color) and not necessarily on performance (flow) characteristics. Palladium particles less than 20 nm can be used in immunoassays. For assays, the particle size needs to be such that the particle flows and stays in solution. The particle should not fall out of solution within the assay. Heating the particles too much and using the wrong ratio of starting materials can lead to particle sizes that are too big.

The nanoparticles used in the present invention are small. These nanoparticles will not spin-down in a centrifuge at 15 K-g. They are not readily separated by gel electrophoresis. They are not readily separated on a sizing gel. And they are not readily determined by dynamic light scattering (DLS).

The reducing agent can affect the particle size. If the pH is too high, the reduction will be too rapid, and the particles will be too large. For example, using formaldehyde in a basic solution will lead to a quick reduction and particles that are too big. In the present invention, glutaraldehyde provides for a slow reduction. It also appears to coat the particles with a coating, which seemingly binds the protein and puts a negative charge on the particles.

The dye system to be used needs to work rapidly at room temperature and form a precipitate that is visually detectable or pleasing. It should be catalytic under physiological conditions, and work in an aqueous medium. An example is described in Conyers et al., "Chromogenic Substrates for Horseradish Peroxidase," Anal. Biochem., 192, (1991) 207-211, the entire contents of which are incorporated herein by reference.

In addition to lateral flow immunoassays, the nanoparticles of the present invention can also be used in dot-blots. Two antigen-antibody interactions were tested: Biotin with Anti-Biotin and DNP with Anti-DNP. The competitive reactions were with DNP-Gelatin or Biotin-Gelatin. Nitrocellulose membranes were spotted with antibody that decreased by a factor of two from left to right. After incubation with biotin/DNP coated NPs, the spots were developed with the dye precursors.

EXAMPLES

Performance

FIG. 4 demonstrates the sensitivity increase possible for catalytic particles compared to colloidal gold. Binding of biomolecules reduces the sensitivity about 2-5 fold so that the ultimate increase over colloidal gold is 30-100 fold.

Palladium nanoparticles developed in dye solution were visible at a concentration of 0.2 ng compared to 100 ng of gold or a 500 times increase. However, a 20-100 times increase is more routinely achieved when a biomolecule is bound as the binding partially reduces the activity.

Preparation of the Colloidal Catalytic Particles—Example for Palladium

To a 7 ml vial is added 2 ml of phosphate buffer pH 11.2 (0.1 M Na2HPO4+0.01 M Na3PO4), 25 µl of 74.6 mM palladium chloride, and 25 µl of 50% glutaric dialdehyde. The resultant homogeneous solution is yellow and has a pH of approximately 10.6. The solution is sealed and then heated to 65° C. for 1-2 hr., cooled, and reheated at 80° C. for an additional 1-2 hr. The solution turns brown and the resultant palladium nanoparticles do not participate even when centrifuged at 12,000 G. Additionally, when dialyzed against 0.05 M sodium carbonate though a Spectra/Par® Dialysis membranes with a 12-14,000 molecular weight cut-off, many of the particles are lost (FIG. 5B). However, they are retained by using a 6-8,000 MWCO membrane. Generally, dialysis did not improve the protein binding nor reduce the amount of protein needed for complete binding. Thus, most preparations were not dialyzed.

FIGS. 5A and 5B show the results from dialysis. FIG. 5A is a picture of the colloid inside the dialysis tubing after dialysis for 4 days in 5.5 L 0.05M NaHCO3 at 4° C. FIG. 5B shows the sensitivity can be compared through serial dilution of the dialyzed material. Dialysis caused about a 4 fold decrease in activity using 6-SK MWCO membranes and an 8-16 fold decrease using 12-14K MWCO membranes. Dialyzed spots spread more than undialyzed spots, possibly due to removal of excess glutaraldehyde.

Gel Elecrophoresis

The particles may be analyzed by gel electrophoresis (FIG. 6). 1% agarose (Biorad, cat #162-0100) in 0.04 M tris-borate buffer (2.6 g boric acid+5.4 g tris(hydroxymethyl)aminomethane base per liter). Running buffer was the same tris borate. The approximately 60×80×4 mm gel at a constant 250V and approximately 13 W power in the positive direction. For loading, 10 µL, of a solution of 100 µL of the colloidal palladium, one drop (ca. 50 µL, of glycerol), and bromophenol blue marker dye was used.

Figure 6:
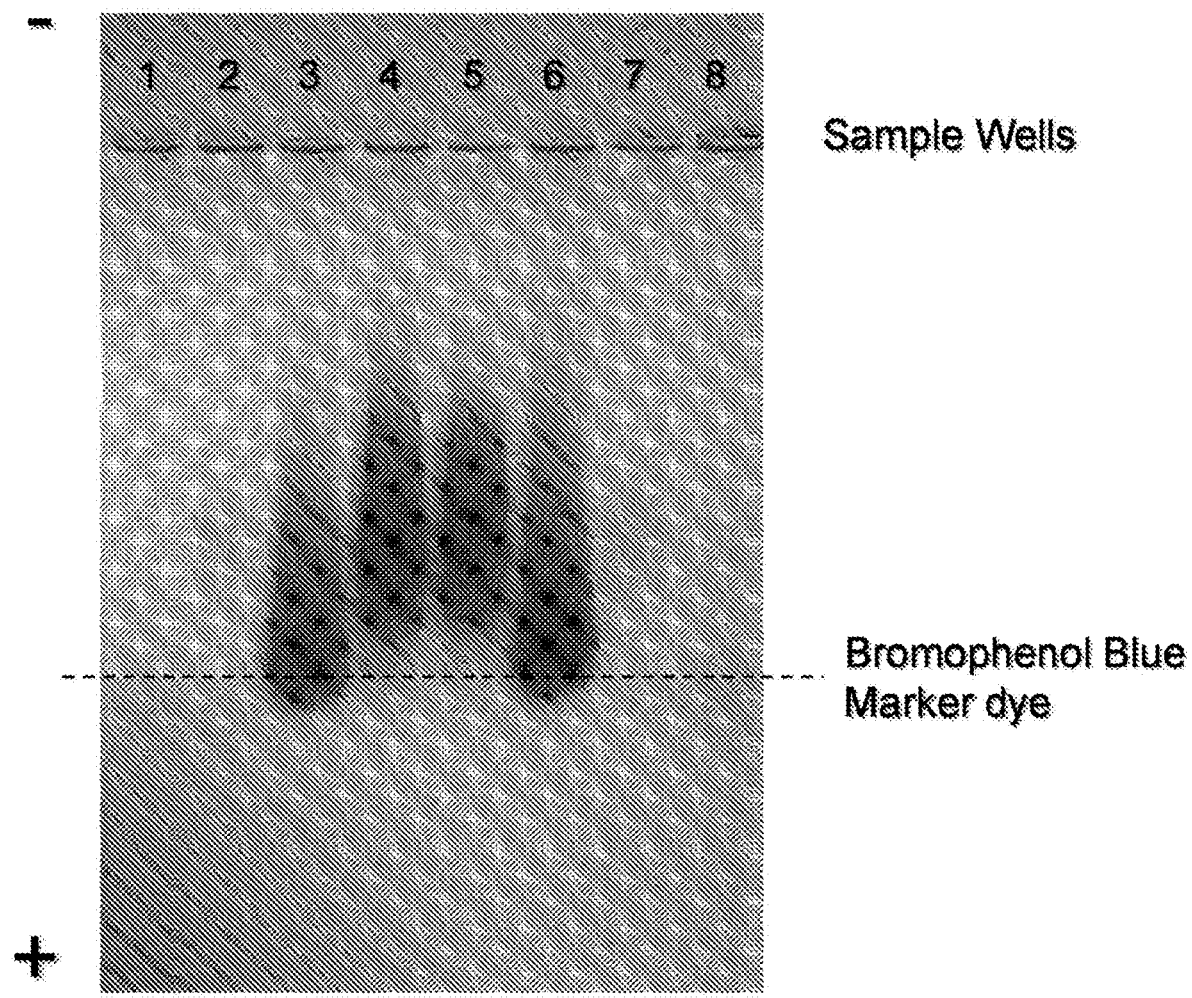
FIG. 6 shows the analysis of various palladium colloids by an agarose gel.

FIG. 6 shows the analysis of various palladium colloids by an agrarose gel. Wells 1 & 8 heated 80° C., 1 hr; wells 2 & 7 heated 80° C., 1 hr+2 µl of 1% bovine serum albumin (BSA); wells 3 & 6 heated 60° C. then 80° C., 1 hr; wells 4 & 5 heated 60° C. then 80° C., 1 hr+2 µl of 1% BSA. The complete binding of the BSA is indicated by the retardation in the gel of the colloidal palladium by the protein. If the initial heating is at 80° C., the resultant colloidal suspension is gray. These particles do not migrate in the gel even in the presence of a protein coating indicating larger particles. The gel was developed by soaking the gel in a solution of ca. 15 mg 4-chloronapthol, ca. 10 mg N,N'-diethylphenylenediamine and 1 pellet of sodium hydroxide in 75 ml of distilled water for 10 minutes. This infuses the gel with the dye precursors, removes the buffer, and allows better color development throughout the thickness of the gel. Then 1 ml of 30% hydrogen peroxide was added to develop the color with colloidal palladium acting as a catalyst. The marker dye diffuses from the gel during color development and its blue color is lost.

Example 1

Labeling of the Colloidal Catalytic Particles with a Biomolecule

Figure 7:
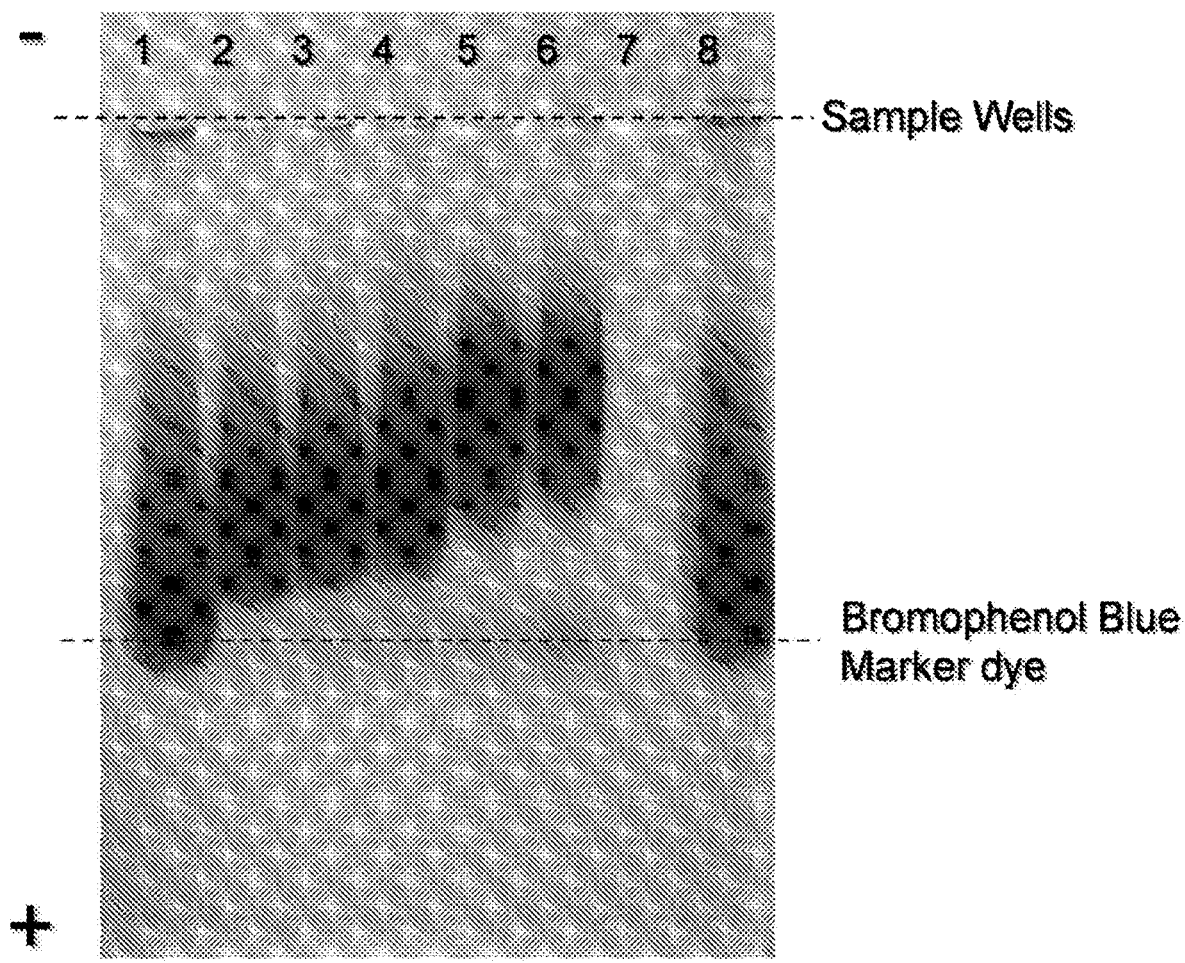
FIG. 7 shows the binding capacity measurements of colloid by agarose gel electrophoresis.

The binding capacity of the colloidal palladium was measured by varying the amount of protein until no changes were observed by gel electrophoresis (FIG. 7). The moles of protein per mole of starting palladium is easily measured. However, the palladium at this stage is in the form of nanoparticles whose size is unknown. If one assumes that the palladium nanoparticles are in the form of a 1.1 nm cube containing approximately 100 atoms and that the size of protein BSA is 14×4×4 nm such that each cube only binds one protein molecule per face (i.e. six molecules of BSA per cube), then the percent expected surface coverage can be calculated as shown in column three of Table 1.

FIG. 7 shows the binding capacity of the colloid by agarose gel electrophoresis. The lanes are described in Table 1. The complete binding of the BSA is indicated by the retardation in the gel of the colloidal palladium by the protein. The gel was analyzed as in FIG. 6.

TABLE 1

Gel description, molar ratio, and surface coverage

| Well Number | Moles of BSA/mole Pd | Surface coverage (%) |
|---|---|---|
| 1 & 8 | 0 | 0 |
| 2 | $3.3 \times 10^{-3}$ | 5.5 |
| 3 | $8.2 \times 10^{-3}$ | 14 |
| 4 | $1.6 \times 10^{-2}$ | 28 |
| 5 | $3.3 \times 10^{-2}$ | 55 |
| 6 | $8.2 \times 10^{-2}$ | 110 |
| 7 | Blank | — |

Alternatively, the protein may bind several palladium nanoparticles, if the nanoparticle is sufficiently small.

Reduction of BSA Labeled Colloidal Palladium with Sodium Borohydride

Figure 8:
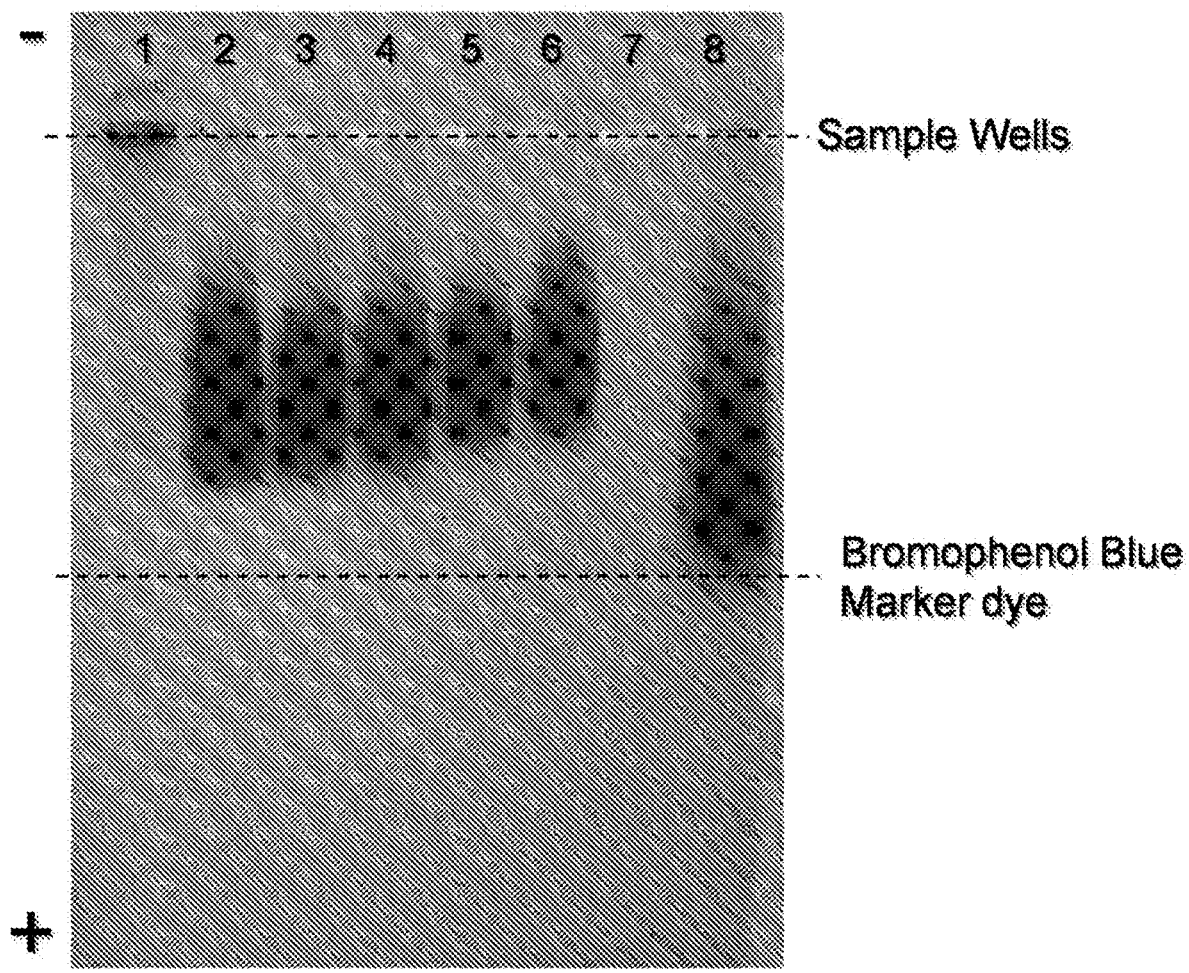
FIG. 8 shows the reduction of the BSA-labeled colloidal palladium with sodium borohydride.
Figure 9:
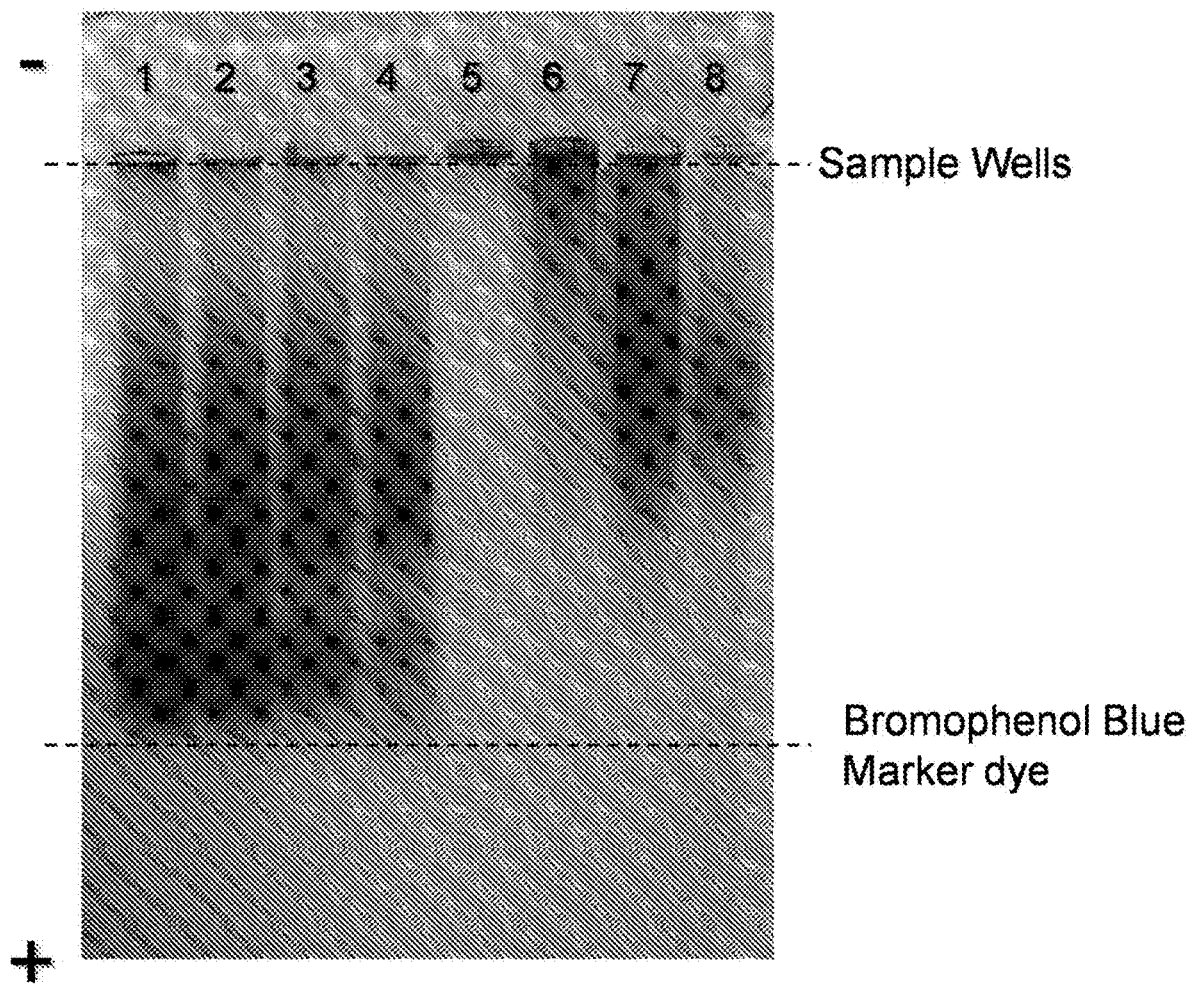
FIG. 9 shows the binding capacity measurement of colloid by agarose gel electrophoresis.

The binding of the protein to the colloidal palladium is assumed to be through formation of an imine with the free remaining aldehydes. This imine can be stabilized by reduction to a secondary amine with sodium borohydride. The effect of protein binding was demonstrated are shown in FIG. 8 using the same samples as in FIG. 7. Although the colloidal palladium is stable for weeks at room temperature, reducing the colloidal palladium in the absence of a protective protein layer causes immediate change in color to black and precipitation of larger *pallidum* particles that do not move in the electrophoresis gel (FIG. 9). Even an incomplete protein layer appears to protect the colloid from precipitation. Based on the similar migration profiles for the unreduced vs. reduced nanoparticles, it does not appear that the reduction increases their size.

FIG. 8 shows the reduction of the BSA-labeled colloidal palladium with sodium borohydride. The sodium borohydride was dissolved in water and immediately added to the premixed samples used for generating FIG. 7. Sodium borohydride solution is added until the bromophenol blue (BPB) marker dye is reduced to a permanent yellow color. The lanes are shown in Table 2. Note the presence of palladium in the sample well #1 indicating that the palladium is too large to enter the agarose gel. The band in the lanes is only slightly tighter than the unreduced labeled colloid.

TABLE 2

Description of lanes for the gel in FIG. 7.

| Well Number | Moles of BSA/mole Pd |
|---|---|
| 1 | 0 |
| 2 | $3.3 \times 10^{-3}$ |

TABLE 2-continued

Description of lanes for the gel in FIG. 7.

| Well Number | Moles of BSA/mole Pd |
|---|---|
| 3 | $8.2 \times 10^{-3}$ |
| 4 | $1.6 \times 10^{-2}$ |
| 5 | $3.3 \times 10^{-2}$ |
| 6 | $8.2 \times 10^{-2}$ |
| 7 | Blank |
| 8 | Non-reduced control with no BSA |

Example 2

Labeling of the Colloidal Catalytic Particles with an Antibody

Antibodies are much larger proteins compared to BSA (MW 150K vs. 66K). The binding capacity of the colloidal palladium was measured by varying the amount of antibody (FIG. 9). However, unlike BSA as in Example 1, less antibody was employed. The moles of protein per mole of starting palladium is easily measured. If one assumes that the palladium nanoparticles are in the form of a 1.1 nm cube containing approximately 100 atoms and that each cube only binds one protein molecule, then the percent expected surface coverage can be calculated as shown in column three of Table 3. One can see that antibodies do not protect the gel from coagulation as well as smaller molecules such as BSA as shown in wells 5-8 of FIG. 9. However, this may be due to lower amounts of antibody such that incomplete coverage was attained.

FIG. 9 shows the binding capacity of colloid by agarose gel electrophoresis. The lanes are described in Table 3. The complete binding of the antibody is indicated by the retardation in the gel of the colloidal palladium by the protein. Wells 5-8 had sodium borohydride addition as in Example 1. Note that insufficient protein allows coagulation upon sodium borohydride addition (well 5-6). The gel was analyzed as in FIG. 6.

TABLE 3

Gel description, molar ratio, and surface coverage

| Well Number | Moles of Antibody/mole Pd | Surface coverage (%) |
|---|---|---|
| 1 & 5 | $7.1 \times 10^{-6}$ | 1.5 |
| 2 & 6 | $1.7 \times 10^{-5}$ | 3.7 |
| 3 & 7 | $3.6 \times 10^{-5}$ | 7.3 |
| 4 & 8 | $7.1 \times 10^{-5}$ | 14.7 |

Example 3

Measuring Excess Protein in the Presence of Colloidal Palladium

Figure 10:
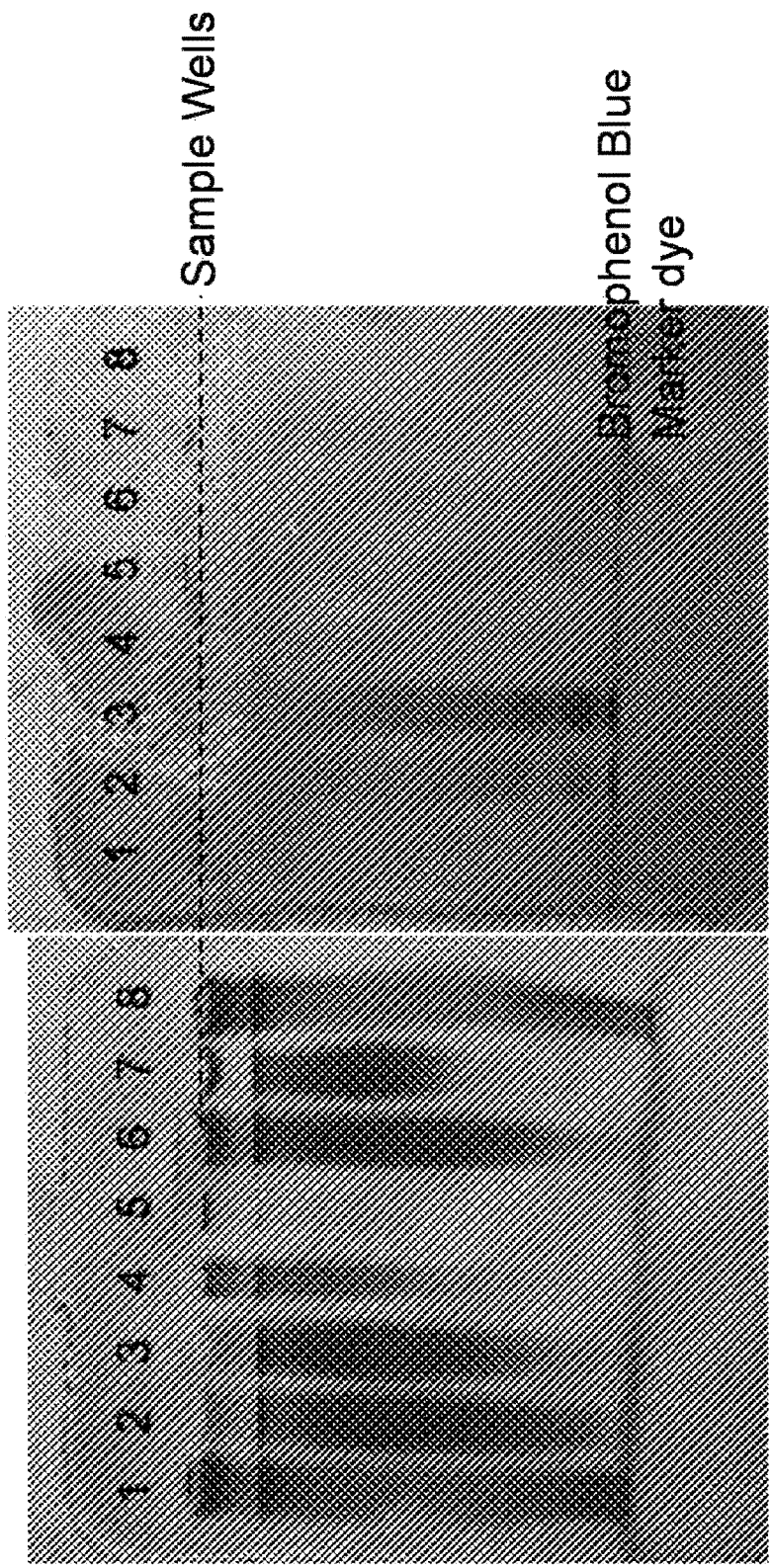
FIG. 10 compares the catalytic detection to Coomassie protein staining.

The gels in FIGS. 7 and 9 demonstrate a method to determine the binding capacity of the nanoparticles with proteins. However, this method cannot determine if all the protein is bound or if only part is bound because of limited number of accessible functionalities on the protein. Polyacrylamide gel electrophoresis was used to determine the free protein by both developing the gel though the catalytic action of the colloidal Pd as staining the proteins with a protein stain (FIG. 10). FIG. 10 shows that the binding of proteins to the colloidal Pd varies with protein type and that BSA is a poorer binding partner than gelatin or non-fat milk. Additionally, FIG. 10 demonstrates the superior detection ability of the colloidal Pd bound to protein compared to a typical protein stain such as Coomassie Blue.

FIG. 10 is a comparison of catalytic detection to Coomassie protein staining. The identity of the well is given in Table 4. A GE Healthcare was loaded with a 4-15 gradient Phast gel and analyzed using a native buffer strip. The gel was developed for Pd colloid, photographed, and then stained with Coomassie Blue and destained in 30-10-60 MeOH-HOAc-Water for protein. The stain-destain removes the dye developed by the colloidal Pd chemistry. Note that the Coomassie Blue shows intense bands in lanes 2 and 3 for free BSA that are not developed by the colloidal Pd compared to essentially no protein staining in the gelatin or non-fat dry milk lanes.

Table 4 lists the amount of protein added to colloidal Pd. Gelatin and non-fat milk are mixtures of proteins with a broad range of molecular weights. Non-fat milk has about 25% of the MW of BSA and gelatin about 80%. Assuming that 50 µl of BSA corresponds to complete coverage as determined in Table 1, if there were equal weight amounts of each protein per nanoparticle sample, then on a mole basis, both the gelatin and non-fat milk should show excess protein.

TABLE 4

Gel description, amount of protein, and surface coverage

| Well Number | Amount of protein added to 100 µL of colloidal Pd |
|---|---|
| 1 & 8 | NPs standard - no protein |
| 2 | 10 µL BSA mg/mL |
| 3 | 50 µL BSA mg/mL |
| 4 | 10 µL Gelatin mg/mL |
| 5 | 50 µL Gelatin mg/mL |
| 6 | 10 µL Non-fat Milk mg/mL |
| 7 | 50 µL Non-fat Milk mg/mL |

Example 4

Use of Colloidal Pd in a LFIA

Figure 11A:
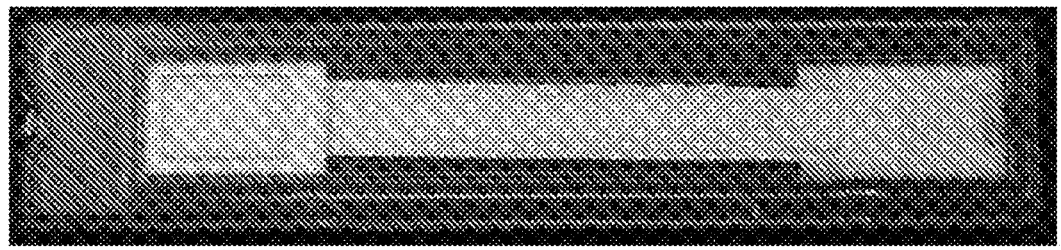
FIG. 11A shows an assembled LFIA.
Figure 11B:
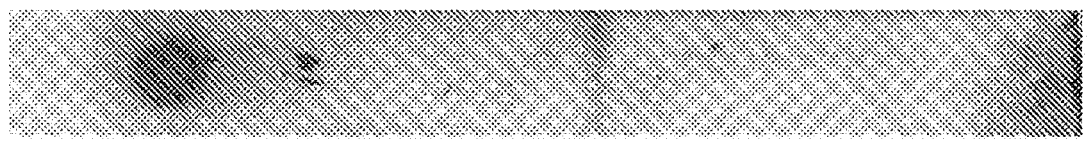
FIG. 11B shows an early LFIA strip showing large amounts of Pd colloid that stayed at origin.
Figure 11C:
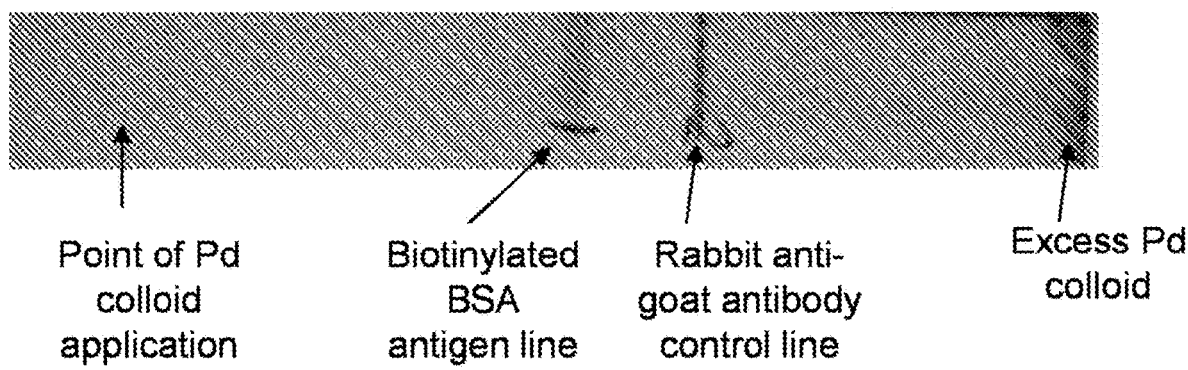
FIG. 11C shows an improved LFIA strip removed from cartridge and developed in a dish.

FIG. 11A shows an example of an assembled LFIA and, FIGS. 11B and 11C show two developed strips. The color of the colloid is insufficient to be readily observed without development. The strips were removed from the cartridge after application of the test fluid and the Pd colloid detected through its catalytic development of the dye. As shown in FIG. 11B, the colloid remained at the origin and more background is observed due to non-specific binding of the colloid. This strip only had the biotinylated BSA antigen line. As shown in FIG. 11C, the improved LFIA strip was blocked with Triton X100 after application of the control and test lines but before applying the Pd colloid. This allowed ready migration of the Pd colloid. The Pd colloid was labeled with goat anti-biotin antibodies as in Example 2. The test line was biotinylated BSA and the control line was rabbit anti-goat antibody, both applied with a printer (Dimatrix DMP-2800 materials printer).

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A method of making and developing catalytic palladium particles, comprising:
   forming a solution of colloidal palladium particles using glutaraldehyde as a reducing agent;
   forming colloidal palladium particles with a glutaraldehyde coating from the solution of colloidal palladium particles;
   binding said colloidal palladium particles with said glutaraldehyde coating with a binding agent to form bonded colloidal palladium particles; and
   catalytically developing the bonded colloidal palladium particles using a visually detectable dye system in a lateral flow immunoassay.

2. The method of claim 1, additionally comprising stabilizing said bonded colloidal palladium particles linkage by reduction.

3. The method of claim 2, wherein said bonded colloidal palladium particles are reduced with sodium borohydride.

4. The method of claim 1, wherein said binding agent comprises a biomolecule.

5. The method of claim 1, wherein said binding agent comprises an antibody.

6. The method of claim 1, wherein said bonded colloidal palladium particles catalytically oxidize N,N'-diethylphenylenediamine which then couples with 4-chloronapthol to make a colored dye.

7. The method of claim 1, wherein said binding agent comprises a protein.

8. The method of claim 1, wherein said binding agent comprises DNA.

9. The method of claim 1, wherein said binding agent comprises RNA.

* * * * *